United States Patent
Eom

(10) Patent No.: US 10,292,646 B2
(45) Date of Patent: May 21, 2019

(54) MOBILE HEALTH CARE DEVICE AND OPERATING METHOD THEREOF

(71) Applicant: SAMSUNG ELECTRONICS CO., LTD., Suwon-si (KR)

(72) Inventor: Kunsun Eom, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 870 days.

(21) Appl. No.: 14/699,536

(22) Filed: Apr. 29, 2015

(65) Prior Publication Data

US 2016/0120460 A1    May 5, 2016

(30) Foreign Application Priority Data

Nov. 4, 2014 (KR) .................. 10-2014-0152085

(51) Int. Cl.
*A61B 5/00* (2006.01)
*A61B 5/0205* (2006.01)
(Continued)

(52) U.S. Cl.
CPC .............. *A61B 5/486* (2013.01); *A61B 5/021* (2013.01); *A61B 5/0205* (2013.01); *A61B 5/0404* (2013.01); *A61B 5/14532* (2013.01); *A61B 5/4872* (2013.01); *A61B 5/6824* (2013.01); *A61B 5/7246* (2013.01); *A61B 5/7282* (2013.01); *A61B 5/742* (2013.01); *A61B 5/7475* (2013.01); *A61B 5/02416* (2013.01); *A61B 5/0488* (2013.01); *A61B 5/053* (2013.01); *A61B 5/1102* (2013.01); *A61B 5/4519* (2013.01);
(Continued)

(58) Field of Classification Search
CPC ....... A61B 5/486; A61B 5/0205; A61B 5/021; A61B 5/0404; A61B 5/14532; A61B 5/4872; A61B 5/6824; A61B 5/7246; A61B 5/7282; A61B 5/742; A61B 5/7475; A61B 5/02416; A61B 5/0488; A61B 5/053; A61B 5/1102; A61B 5/4519; A61B 5/4806; A61B 5/4866; A61B 5/4875

See application file for complete search history.

(56) References Cited

U.S. PATENT DOCUMENTS 6,595,929 B2 *   7/2003   Stivoric ............... A61B 5/0008
                                                        600/549
8,398,546 B2 *   3/2013   Pacione ................. A61B 5/411
                                                        128/920
(Continued)

FOREIGN PATENT DOCUMENTS

JP         2013-109700 A        6/2013
KR      10-2011-0043828 A       4/2011
(Continued)

*Primary Examiner* — Christopher A Flory
*Assistant Examiner* — Shirley X Jian
(74) *Attorney, Agent, or Firm* — Sughrue Mion, PLLC

(57) ABSTRACT

Provided are a health care device and a method of operating the health care device. The method includes: detecting, by the health care device, biosignal information of a user through skin of the user; obtaining health status information of the user by using the detected biosignal information; providing a task of the user for improving a health status, according to the obtained health status information; and monitoring whether the user achieves the provided task.

16 Claims, 15 Drawing Sheets

(51) Int. Cl.
*A61B 5/145* (2006.01)
*A61B 5/021* (2006.01)
*A61B 5/0404* (2006.01)
*A61B 5/11* (2006.01)
*A61B 5/0488* (2006.01)
*A61B 5/053* (2006.01)
*A61B 5/024* (2006.01)

(52) U.S. Cl.
CPC ........... *A61B 5/4806* (2013.01); *A61B 5/4866* (2013.01); *A61B 5/4875* (2013.01)

(56) References Cited

U.S. PATENT DOCUMENTS

| | | | | |
|---|---|---|---|---|
| 8,734,296 | B1 * | 5/2014 | Brumback | G06F 19/3406 482/8 |
| 8,944,958 | B1 * | 2/2015 | Brumback | G06F 19/3406 482/8 |
| 9,144,381 | B2 * | 9/2015 | Rosen | A61B 5/0002 |
| 9,211,417 | B2 * | 12/2015 | Heldman | A61B 5/1101 |
| 9,238,142 | B2 * | 1/2016 | Heldman | A61B 5/1101 |
| 9,522,278 | B1 * | 12/2016 | Heldman | A61B 5/1101 |
| 9,717,920 | B1 * | 8/2017 | Heldman | A61B 5/1101 |
| 9,836,581 | B2 * | 12/2017 | Madan | G06F 19/3418 |
| 10,092,754 | B1 * | 10/2018 | Heldman | A61B 5/1101 |
| 2002/0183646 | A1 * | 12/2002 | Stivoric | A61B 5/0008 600/549 |
| 2003/0036683 | A1 * | 2/2003 | Kehr | G06F 19/325 600/300 |
| 2005/0113650 | A1 * | 5/2005 | Pacione | A61B 5/411 600/300 |
| 2012/0072231 | A1 * | 3/2012 | Mayer | G06F 19/3456 705/2 |
| 2012/0316471 | A1 * | 12/2012 | Rahman | A61B 5/0008 600/595 |
| 2013/0158367 | A1 * | 6/2013 | Pacione | A61B 5/0022 600/301 |
| 2014/0052475 | A1 * | 2/2014 | Madan | G06F 19/3418 705/3 |
| 2014/0074180 | A1 * | 3/2014 | Heldman | A61B 5/1101 607/45 |
| 2015/0186609 | A1 * | 7/2015 | Utter, II | A61B 5/0022 600/301 |
| 2016/0081581 | A1 | 3/2016 | Eom et al. | |
| 2016/0120460 | A1 * | 5/2016 | Eom | A61B 5/486 600/301 |

FOREIGN PATENT DOCUMENTS

KR 10-2013-0140589 A 12/2013
KR 10-2014-0056752 A 5/2014

* cited by examiner

MOBILE HEALTH CARE DEVICE AND OPERATING METHOD THEREOF

CROSS-REFERENCE TO RELATED APPLICATION

This application claims priority from Korean Patent Application No. 10-2014-0152085, filed on Nov. 4, 2014 in the Korean Intellectual Property Office, the disclosure of which is incorporated herein in its entirety by reference.

BACKGROUND

1. Field

Apparatuses and methods consistent with exemplary embodiments relate to a mobile health care device and an operating method thereof.

2. Description of the Related Art

Due to developments in medical science and the increase in average life expectancy, interest in health care and medical devices is on the rise. The medical devices include various devices used in hospitals or medical examination centers, as well as medium-size or small devices provided at public facilities, or miniature medical devices and health care devices that may be possessed or carried by individuals.

SUMMARY

Aspects of one or more exemplary embodiments provide an apparatus and a method of providing a task to a user based on biosignal information.

Additional aspects will be set forth in part in the description which follows and, in part, will be apparent from the description, or may be learned by practice of exemplary embodiments.

According to an aspect of an exemplary embodiment, there is provided a method of operating a health care device, the method including: detecting, by the health care device, biosignal information of a user through skin of the user; obtaining health status information of the user by using the detected biosignal information; providing a task of the user for improving a health status, according to the obtained health status information; and monitoring whether the user achieves the provided task.

The task may be provided in response to the health status information being within a reference range.

The reference range may include an abnormal range corresponding to abnormal health status information.

The providing the task may include: displaying one or more details of the provided task; and modifying at least one of the displayed one or more details according to an input of the user.

The modifying may include, in response to a modification according to the input of the user being outside a modifiable range, providing a notification indicating that the modification is outside the modifiable range.

The modifying may include, in response to a modification according to the input of the user being outside a modifiable range, determining a value of the one or more details to be a boundary value of the modifiable range.

The one or more details may include at least one of a type, a cycle, an execution amount, a start time, and an execution duration of the provided task.

The monitoring may include: receiving, from the user, a user response regarding the provided task; and calculating an achievement rate of the provided task based on the received user response.

The monitoring may further include providing an execution start notification regarding the provided task.

The method may further include calculating a correlation between the provided task and the health status by using the calculated achievement rate.

The method may further include, in response to the calculated correlation being below a reference value, finishing the monitoring.

The biosignal information may be detected in a non-invasive manner.

The biosignal information may include at least one of blood glucose, cholesterol, bio-impedance, electrocardiogram (ECG), ballistocardiogram (BCG), photoplethysmograph (PPG), and electromyogram (EMG) of the user; and the health status information may include at least one of, body fat, skeletal muscles, visceral fat, basal metabolic rate (BMR), a hydration level, triglyceride (TG), low density lipoprotein (LDL), high density lipoprotein (HDL), a ratio between LDL and HDL, a stress index, maximum blood pressure, minimum blood pressure, a fasting blood sugar level, a blood glucose increase rate, a total amount of cholesterol, and a blood glucose health index of the user.

The provided task may include at least one of an exercise habit, an eating habit, a sleeping habit, a medicine intake habit, and a fluid intake habit.

According to an aspect of another exemplary embodiment, there is provided a health care device including: a sensor configured to contact skin of a user and to detect biosignal information of the user through the skin; a processor configured to obtain health status information of the user by using the detected biosignal information; an output unit configured to output a task of the user for improving a health status, according to the obtained health status information; and a controller configured to monitor whether the user achieves the provided task.

The controller may be configured to output, via the output unit, one or more details of the provided task, and to modify at least one detail selected from among the output one or more details according to an input of the user.

The controller may be configured to receive, from the user, a user response regarding the provided task, and to calculate an achievement rate of the task based on the received user response; and the controller may be configured to calculate a correlation between the provided task and the health status by using the calculated achievement rate, and in response to the calculating correlation being below a reference value, the controller may be configured to finish monitoring.

The sensor may be a wristband type device that is attachable to and detachable from a wrist of the user.

The health care device may further include at least one of a first module configured to provide an execution start notification regarding the provided task and a second module configured to receive a user response regarding the provided task.

In response to the task negatively affecting another type of health status other than the health status, the controller may be configured to provide a notification indicating that the other type of health status has been negatively affected.

According to an aspect of another exemplary embodiment, there is provided a computer-readable recording medium having recorded thereon a program executable to perform the above method.

BRIEF DESCRIPTION OF THE DRAWINGS

These and/or other aspects will become apparent and more readily appreciated from the following description of exemplary embodiments, taken in conjunction with the accompanying drawings in which.

DETAILED DESCRIPTION

Figure 1A:
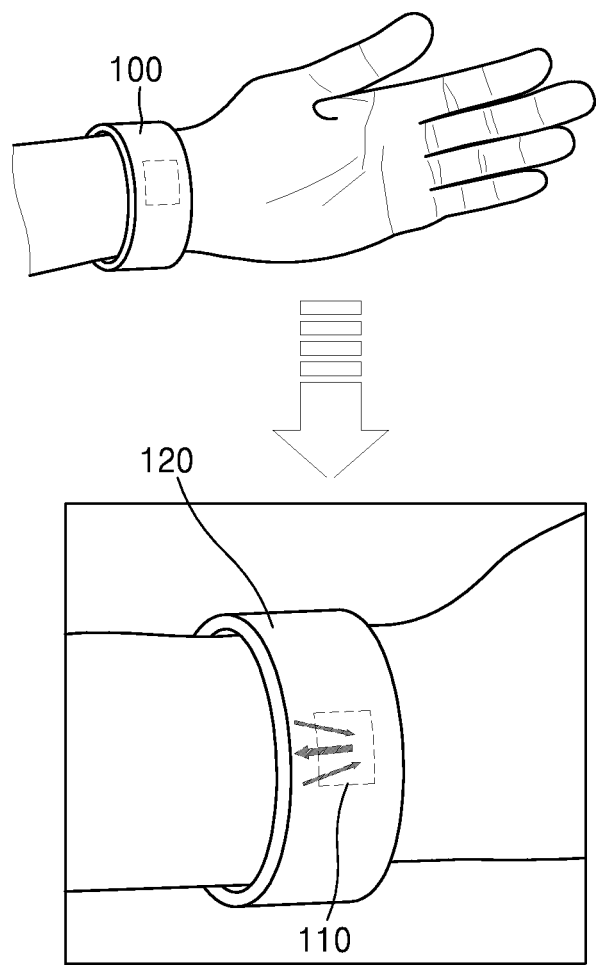
FIGS. 1A and 1B are diagrams illustrating a concept of a health care device that is worn on a wrist, according to an exemplary embodiment.

The terms used in the description of exemplary embodiments are selected as general terms used widely. However, in some cases, terms arbitrarily selected by the applicant may be used, and in such cases the meanings are provided in the corresponding detailed description section, so that exemplary embodiments may be understood not by literal meanings of the terms, but by given meanings of the terms.

Throughout the specification, it will also be understood that when an element is referred to as being "connected to" another element, it can be directly connected to the other element, or electrically connected to the other element while intervening elements may also be present. It will be further understood that the terms "comprises" and/or "comprising" used herein specify the presence of stated features or components, but do not preclude the presence or addition of one or more other features or components. In addition, the terms such as "unit," "-er (-or)," and "module" described in the specification refer to an element for performing at least one function or operation, and may be implemented in hardware, software, or the combination of hardware and software.

The terms "comprise" or "includes" should not be construed as necessarily including all elements or operations described in the specification. It will be understood that some elements and some operations may not be included, or additional elements or operations may be further included.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. In addition, all exemplary embodiments that may be easily derived by one of ordinary skill in the art from the detailed description and exemplary embodiments are construed as being included in the scope of the present inventive concept. Expressions such as "at least one of," when preceding a list of elements, modify the entire list of elements and do not modify the individual elements of the list.

A health care device according to an exemplary embodiment may be a device that may be carried by a user, such as a wearable device. The health care device may be one selected from a watch type device, a wristband type device, a ring type device, a hair band type device, a necklace type device, a gasses type device, etc., or a combination thereof, and includes communication functions and data processing functions. Although the health care device is described as a watch type device or a wristband type device in the present exemplary embodiments, it is understood that one or more other exemplary embodiments are not limited thereto.

Also, the health care device may be provided as a single housing or a plurality of housings. When the health care device is provided as a plurality of housings, a plurality of components may be wired or connected wirelessly. For example, the health care device may be distinguished into a first device that may be worn on a wrist of a user and includes a sensor that detects biosignal information, and a second device that processes the biosignal information. The health care device may be provided as a portion of a device performing different functions, such as a mobile terminal.

Figure 1B:
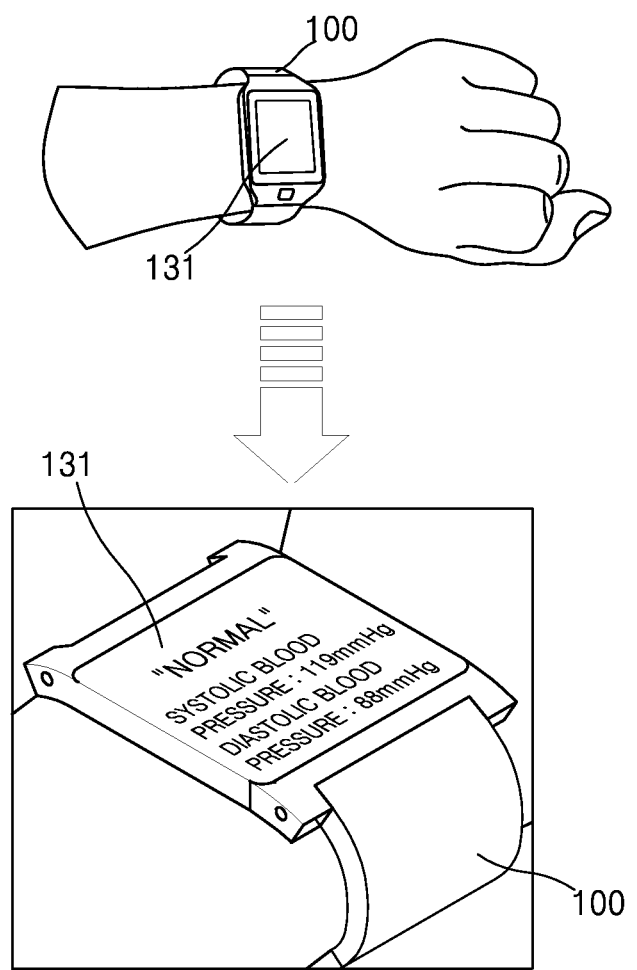

FIGS. 1A and 1B are diagrams illustrating a concept of a health care device 100 that is worn on a wrist, according to an exemplary embodiment. Referring to FIG. 1A, the health care device 100 may include a sensor 110 that detects biosignal information via a wrist of the user when the health care device 100 is worn thereon. Also, the health care device 100 may include a processor that processes the biosignal information. The processor may obtain heath status information of the user from the biosignal information that is received from the sensor 110.

Referring to FIG. 1B, the user may receive the health status information, generated in the processor, via a screen shown on a display unit 131 (e.g., display) of the health care device 100 worn on the wrist. For example, when the health status information includes blood pressure information regarding the user, the display unit 131 may display at least one of minimum blood pressure, maximum blood pressure, systolic blood pressure, diastolic blood pressure values, information regarding whether current blood pressure status is normal or abnormal, and blood vessel flexibility information. In addition, the health care device 100 according to an exemplary embodiment may consistently manage a health status of the user by providing tasks for improving the health status of the user based on the health status information of the user.

Figure 2:
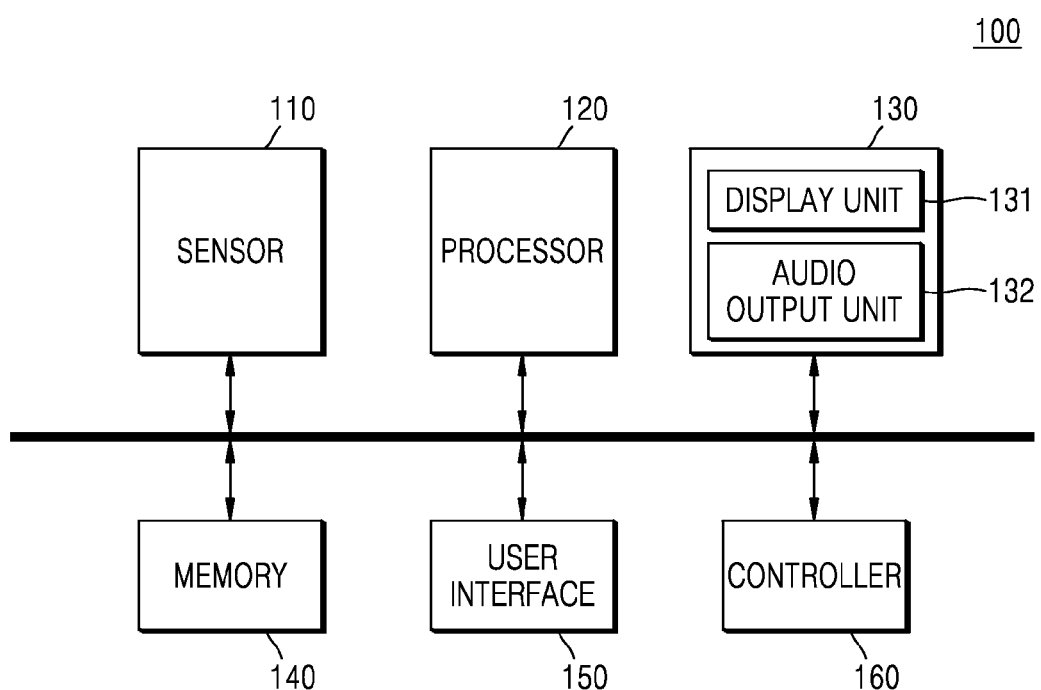
FIG. 2 is a block diagram illustrating a health care device according to an exemplary embodiment.

FIG. 2 is a block diagram illustrating the health care device 100 according to an exemplary embodiment. As shown in FIG. 2, the health care device 100 may include the sensor 110 that detects the biosignal information of the user, a processor 120 that obtains health status information of the user by using the biosignal information received from the sensor 110, an output unit 130 (e.g., outputter or output device) that outputs the obtained health status information, a memory 140 that stores a program that may be used in the health care device 100, a user interface 150 that receives user commands, and a controller 160 that controls components in the health care device 100.

The user may be an object from which biosignal information is detected and to which a health management service is provided. The user may be a human or an animal. The biosignal information is a unique signal generated from the user, for example, a signal according to motions of a certain object (e.g., heart or muscles) of the user such as electrocardiogram (ECG), ballistocardiogram (BCG), photoplethysmograph (PPG), electromyogram (EMG), and blood pressure. Furthermore, the biosignal information may be information regarding a material in the user such as blood glucose (e.g., a fasting blood sugar level or a blood glucose increase rate), cholesterol, or bio-impedance.

The health status information may be obtained by using or according to the biosignal information. For example, the biosignal information such as ECG or PPG may be used to obtain the health status information such as at least one of maximum blood pressure, minimum blood pressure, and a blood vessel health index. Also, biosignal information such as bio-impedance may be used to obtain health status information of body components, for example, at least one of body fat, skeletal muscles, visceral fat, a basal metabolic rate (BMR), hydration level, stress index, triglyceride (TG), low density lipoprotein (LDL), high density lipoprotein (HDL), and a ratio between LDL and HDL. Also, blood glucose may be used to obtain information regarding at least one of a fasting blood sugar level and a blood glucose increase rate.

The sensor 110 may detect the biosignal information of the user. The sensor 110 may be worn on a wrist, the chest, an ankle, or an abdominal region of the user, although it is understood that one or more other exemplary embodiments are not limited thereto. The sensor 110 may detect the biosignal information in a non-invasive manner. For example, the sensor 110 may include a plurality of electrodes, and at least some of the plurality of electrodes may contact the user when the user is wearing the health care device 100. Then, the sensor 110 may detect the biosignal information by detecting electrical properties, for example, a change in the bio-impedance, according to a change in the biosignal information. Furthermore, the sensor 110 may detect the biosignal information by using signals reflected from the user when light is emitted on the user, and/or by using magnetic signals or pressure.

The sensor 110 may include a motion sensor that detects motions of the user. The motion sensor may include at least one of an acceleration sensor, a gyro sensor, and a terrestrial magnetic sensor.

The processor 120 may obtain (e.g., determine) the health status information by using the biosignal information. The processor 120 may generate the health status information as an image or text. In addition, the processor 120 may generate the health status information as an audio frequency. The processor 120 may be formed or provided as a single microprocessor module or a combination of two or more microprocessor modules. In other words, the processor 120 is not limited to a predetermined form.

The processor 120 may use different methods to obtain different types of health status information depending on the type of the biosignal information. For example, when the biosignal information is bio-impedance, the processor 120 may obtain body components or indices of the user by using the bio-impedance. The body components may include at least one of body fat, body mass, skin properties (for example, hydration level), muscle strength, existence of edema, an amount of skeletal muscles, an amount of muscles, an obesity index, a body composition ratio, and visceral fat of the user. Furthermore, the processor 120 may obtain the body components by using not only the bio-impedance, but also user information. The user information may include at least one of age, weight, height, and gender of the user.

Also, when the biosignal information is ECG signals according to motions of the heart, the processor 120 may obtain biosignal information waveforms from the biosignal information, and obtain health status information such as maximum blood pressure and minimum blood pressure from the biosignal information waveforms. In order to obtain the biosignal information waveforms, the processor 120 may amplify the ECG signals, and filter the amplified ECG signals by using a far infrared (FIR) bandpass filter. Also, the processor 120 may detect peaks from the filtered ECG signals, perform adaptive filtering on the detected peaks, and thereby obtain the biosignal information waveforms.

The output unit 130 may output the health status information of the user, a task for improving the health status, and a notification for achieving the task. The output unit 130 may include at least one of the display unit 131 (e.g., display) that displays the above-described information as an image or text and an audio output unit 132 (e.g., speaker, audio output device, audio output interface, audio outputter, etc.) that outputs the above-described information as an audio frequency. Furthermore, the output unit 130 may additionally include a vibrator that outputs a notification for executing the task by vibrating or an emission unit (e.g., emitter) that emits light.

The display unit 131 may display a user interface (UI) or a graphic UI (GUI) for displaying a user protocol of the health care device 100, the health status information of the user, the task for improving the health status, and the notification for executing the task. The display unit 131 may include at least one of a liquid crystal display (LCD), a thin film transistor (TFT) LCD, an organic light-emitting diode (OLED) display, a flexible display, a three-dimensional (3D) display, an active matrix OLED (AMOLED) display, etc. Also, two or more display units may be included depending on structures of the health care device 100.

The display unit 131 and a touch pad for receiving inputs of the user may form a mutual layer structure and thus constitute a touch screen. When the display unit 131 and the touch pad form a mutual layer structure and thus constitute the touch screen, the display unit 131 may be used as not only an output device, but also an input device.

The memory 140 may store data generated as operations of the health care device 100 are performed. The memory 140 according to an exemplary embodiment may be a typical storage medium, and may include a hard disk drive (HDD), read-only memory (ROM), random access memory (RAM), flash memory, and a memory card.

The user interface 150 may receive an input for manipulating the health care device 100 from the user, and output at least one of the biosignal information and the user information which are processed by the health care device 100. The user interface 150 may include at least one of a button, a keypad, a switch, a dial, a touch interface, and a voice recognition interface, which may be used by the user to directly manipulate the health care device 100. The user interface 150 may include a display unit 131 for displaying an image and may be formed or provided as a touch screen.

The controller 160 may control operations of the health care device 100. For example, the controller 160 may control the sensor 110 such that the biosignal information is obtained. Also, the controller 160 may determine whether the obtained health status information is normal or abnormal, and provide the determination result to the user via the display unit 131.

The health care device 100 may include various components performing various functions other than the above-described components, such as a communication unit (e.g., communicator) that may communicate with external devices.

Figure 3:
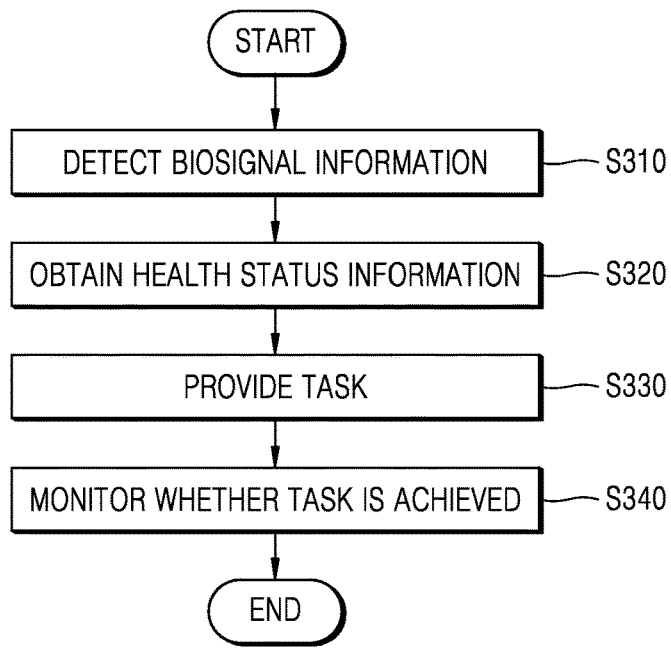
FIG. 3 is a flowchart illustrating a method of operating a health care device, according to an exemplary embodiment.

FIG. 3 is a flowchart illustrating a method of operating the health care device 100, according to an exemplary embodiment. Referring to FIG. 3, the sensor 110 may detect (e.g., sense or obtain) biosignal information (operation S310). The biosignal information is related to health and may be detected through skin of a user. The sensor 110 may detect the biosignal information in a non-invasive manner. For example, the sensor 110 may detect biosignal information of at least one of bio-impedance, ECG, BCG, PPG, EMG, blood glucose, and cholesterol via the skin of the user by using a plurality of electrodes and/or a light source.

The processor 120 may obtain health status information of the user by using the biosignal information detected by the sensor 110 (operation S320). The processor 120 may obtain a plurality of pieces of health status information by using a single piece of biosignal information. For example, when the biosignal information is bio-impedance of the user, the processor 120 may obtain health status information of the user, such as at least one of body fat, skin properties (for example, hydration level), muscle strength, existence of edema, an amount of skeletal muscles, an amount of muscles, an obesity index, a body composition ratio, and visceral fat of the user, by using the bio-impedance. Furthermore, when the biosignal information is ECG, BCG, PPG, or EMG of the user, the processor 120 may obtain health status information such as at least one of maximum blood pressure, minimum blood pressure, blood vessel flexibility, and a cardiac disorder. Blood glucose and cholesterol may be included in the biosignal information as well as the health status information.

The controller 160 may provide a task for improving a health status of the user (operation S330). The task may be provided when the health status information is within a reference range (e.g., a predetermined or preset range), and may not be provided when the health status information is outside the reference range. The task is an action that is to be executed by the user to cause the health status information to be outside the reference range, and the task may have periodicity. For example, the task may be related to an exercise habit, an eating habit, a sleeping habit, and a nutrition intake habit. A method of providing the task will be described with reference to FIG. 4. According to another exemplary embodiment, the task may be provided when the health status information is outside a reference range (e.g., a predetermined or preset range), and may not be provided when the health status information is within the reference range.

The controller 160 may monitor whether the user has achieved the task (operation S340). The controller 160 may monitor at least one of an achievement rate of the user, whether the health status has been improved based on an achievement of the user, and a correlation between the task and the health status.

Figure 4:
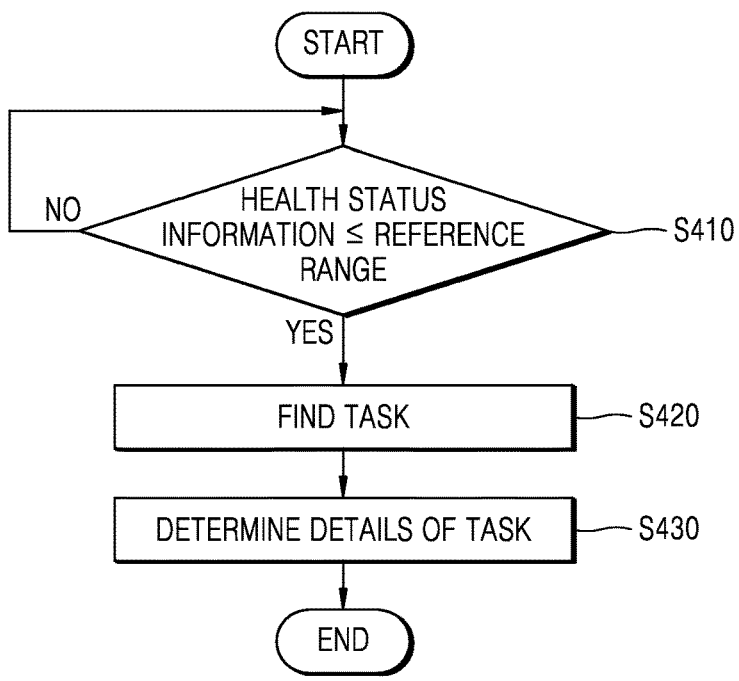
FIG. 4 is a flowchart illustrating a method of providing a task of a user, according to an exemplary embodiment.

FIG. 4 is a flowchart illustrating a method of providing a task of a user, according to an exemplary embodiment. FIGS. 5A to 5D are referential diagrams illustrating a method of providing tasks of a user, according to an exemplary embodiment.

Referring to FIGS. 4 and 5A to 5D, the controller 160 may determine whether the health status information is within a reference range (operation S410). The reference range may not only include a range in which the health status information is abnormal, but also a range in which the health status information is normal but has a possibility of becoming abnormal. The reference range may be prestored in the memory 140 according to each type of health status. However, it is understood that one or more other exemplary embodiments are not limited thereto. For example, according to another exemplary embodiment, the reference range may be set by the user. By way of example, when an abnormal range of cholesterol is 220 or above, a reference range of cholesterol may be stored as 200 or above in the memory 140. However, when the user wants to manage cholesterol from 185 or above, the reference range of cholesterol may be set by the user as 185 or above.

When the health status information is within the reference range (operation S410—Yes), a task for improving the health status may be found or obtained (operation S420). A task related to each type of health status may be stored in the memory 140 as metadata. The controller 160 may read or obtain a task that corresponds to the health status from the memory 140. However, it is understood that one or more other exemplary embodiments are not limited thereto. For example, according to another exemplary embodiment, the health care device 100 may access an external device, for example, a web server or a health management server provided by a medical institution, via a network, and search for the task that corresponds to the health status.

Also, the controller 160 may determine details of the task (operation S430). Since the task requires the user to periodically execute an action, the details of the task may include at least one of a type, a cycle, intensity, and a start time of the task. The term "intensity" refers to execution duration (e.g., exercise time) or an execution amount (e.g., an amount of food).

When there are a plurality of tasks, the controller 160 may display a task list that includes the plurality of tasks. Also, the controller 160 may select at least one task from the task list according to an input of the user. For example, when health status information indicates that the user is overweight due to body fat, tasks may be related to at least one of an exercise habit, an eating habit, a medicine intake habit, a sleeping habit, and a fluid intake habit.

Figure 5A:
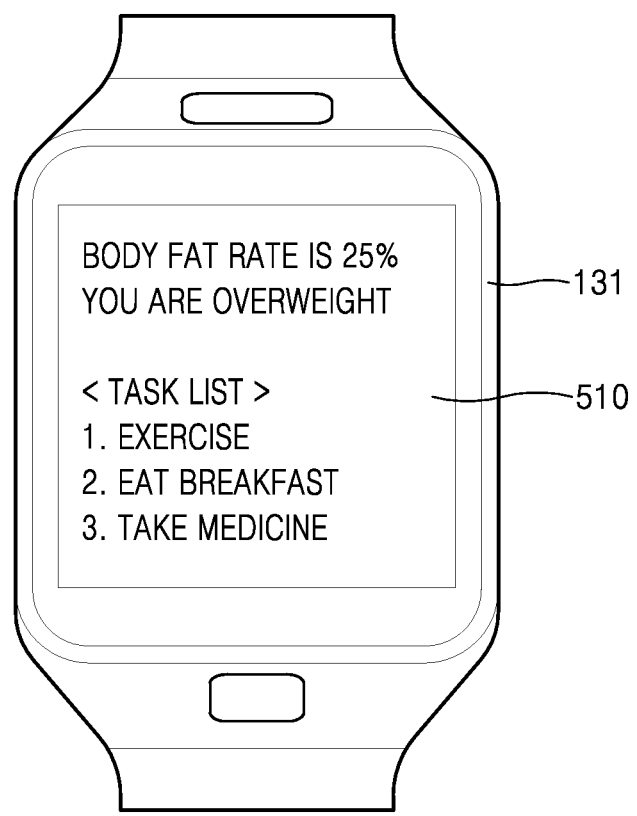
FIGS. 5A to 5D are referential diagrams illustrating a method of providing a task of a user, according to an exemplary embodiment.
Figure 5B:
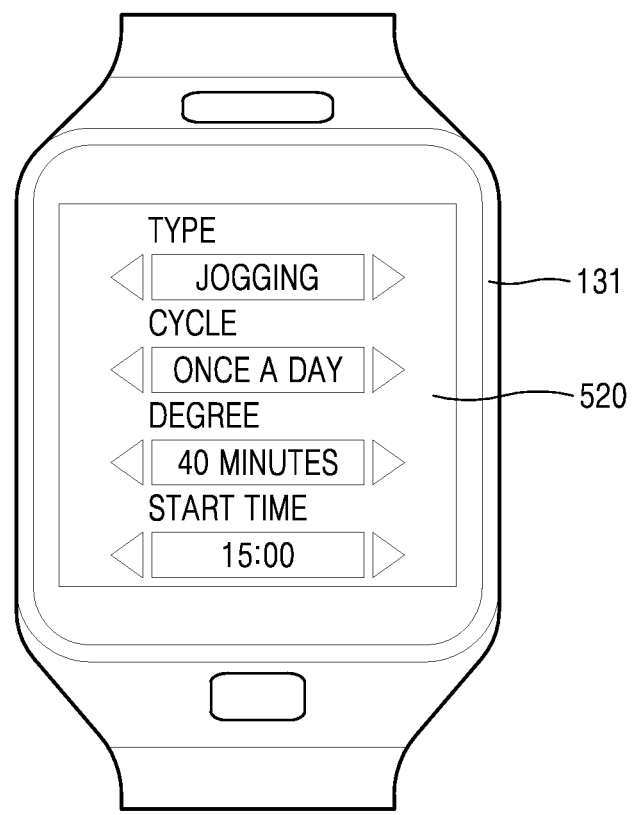

As shown in FIG. 5A, the controller 160 may display a task list 510 on the display unit 131. In FIG. 5A, the user may select exercise. A plurality of exercises may be appropriate for losing weight. Then, the controller 160 may display details related to the selected task, and determine details of the selected task according to an input of the user. For example, as shown in FIG. 5B, details 520, including an exercise type, an exercise cycle, an exercise time, and an exercise start time that are appropriate for losing weight, may be displayed. When a plurality of exercises are appropriate for losing weight, the controller 160 may provide in advance an exercise type, an exercise cycle, an exercise time, and an exercise start time that are effective (e.g., most effective) for losing weight.

Figure 5C:
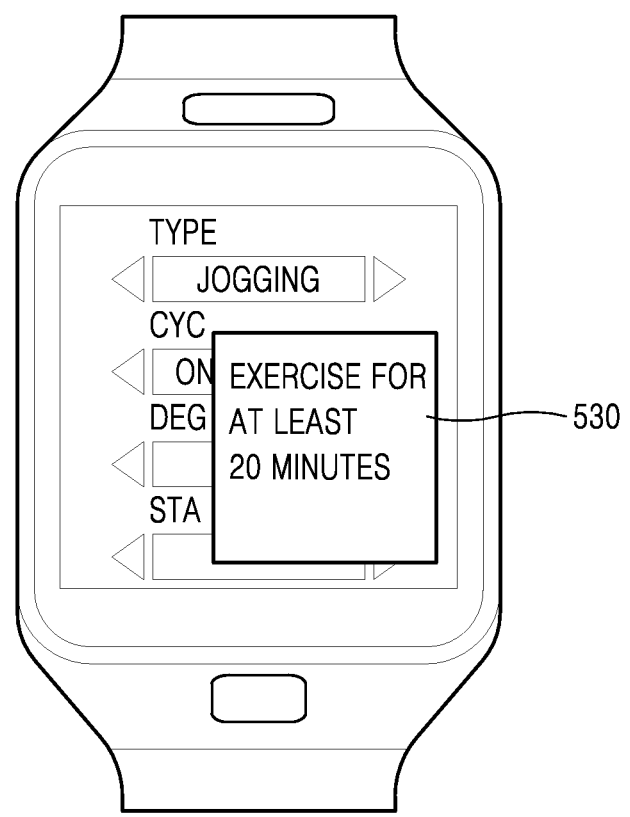

Furthermore, the details 520 may be adjusted by an input of the user. However, an adjustment range of the details 520 may be limited to a predetermined range, e.g., a range that may improve the health status when achieved. For example, the user may adjust the exercise time. However, when an exercise time adjusted by the user is outside a modifiable range, as shown in FIG. 5C, the controller 160 may provide a notification 530 indicating that the health status may not be improved at the adjusted exercise time.

Figure 5D:
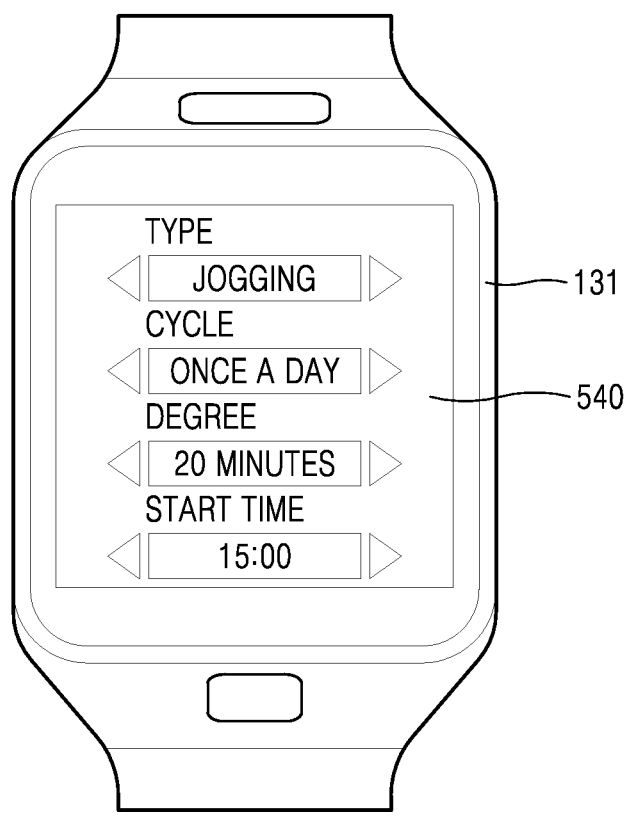

The controller 160 may determine a task to be a boundary value of a modifiable range. For example, even when the user has set an exercise time to 15 minutes, the controller 160 may provide the notification 530 as shown in FIG. 5C, and determine details 540 such that the exercise time is 20 minutes, that is, a boundary value of the exercise time, as shown in FIG. 5D.

Figure 6:
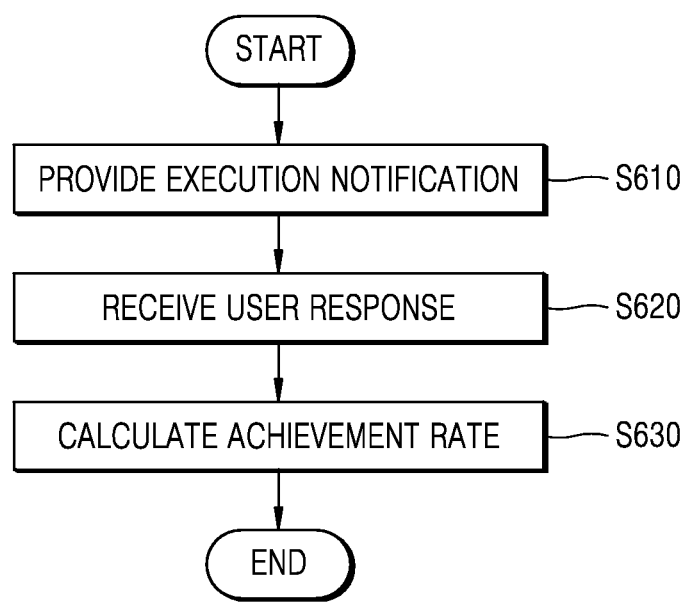
FIG. 6 is a flowchart illustrating a method of monitoring whether a task is achieved.
Figure 7A:
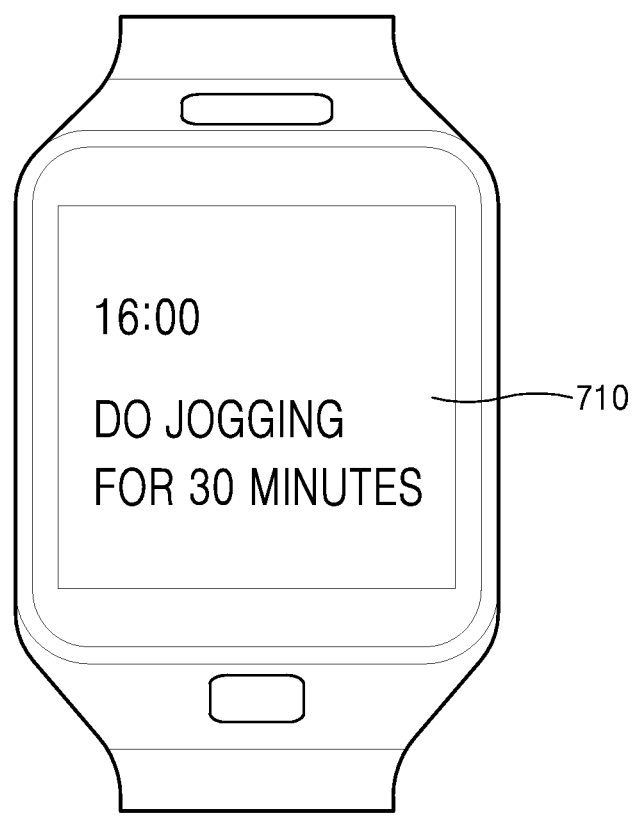
FIGS. 7A and 7B are referential diagrams illustrating a method of monitoring a task.
Figure 7B:
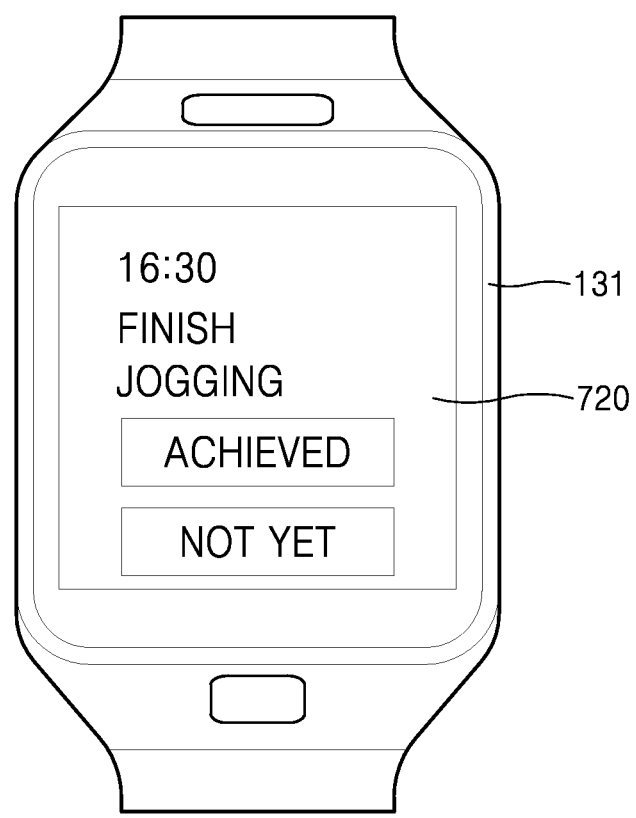

FIG. 6 is a flowchart illustrating a method of monitoring whether a task is achieved. FIGS. 7A and 7B are referential diagrams illustrating a method of monitoring a task.

Referring to FIGS. 6, 7A, and 7B, the controller 160 may provide an execution notification (operation S610). The controller 160 may provide the execution notification at a start time included in details of a task. The notification may be provided as at least one of an image or a text, and/or via an audio frequency, vibration, light emission, temperature change, or pressure change. For example, as shown in FIG. 7A, the controller 160 may provide a notification 710 as text on the display unit 131. However, it is understood that one or more other exemplary embodiments are not limited thereto. For example, according to another exemplary embodiment, a notification may not be provided according to a selection or a setting of the user.

The controller 160 may receive a user response regarding the task from the user (operation S620). As shown in FIG. 7B, the controller 160 may provide a notification 720 regarding a task finish time. The controller 160 may receive the user response regarding the task when the user selects a key that indicates "achieved" or "not yet." Alternatively, the controller 160 may receive the user response from the user by using the sensor 110 that corresponds to the task. The controller 160 may activate the sensor 110 that corresponds to the task at a task start time. For example, when a task is "exercise" the controller 160 may activate a motion sensor. Also, the user response of the user may be received from a detection result of the motion sensor. For example, when a task includes an exercise for a certain distance or for a certain number of steps, the user response may be received from a detection result of a sensor that senses a distance or a number of steps achieved by a user.

The controller 160 may calculate an achievement rate by using the user response of the user (operation S630). The controller 160 may calculate the achievement rate as a function of time, or as an actual achievement amount relative to an entire amount to be achieved.

Figure 8:
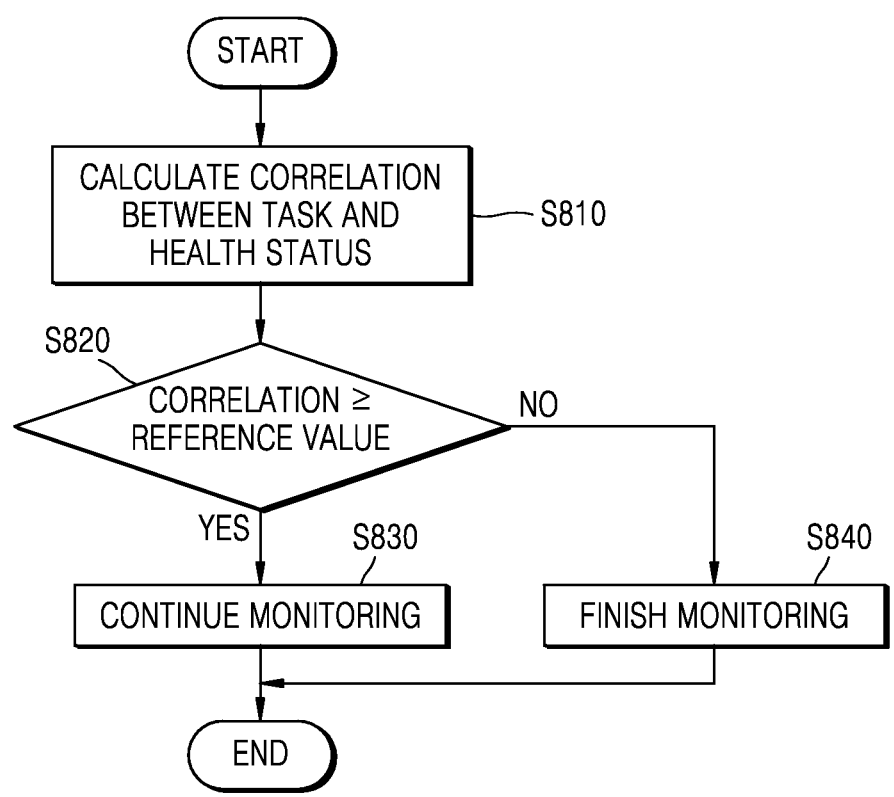
FIG. 8 is a flowchart illustrating a method of operating a health care device that evaluates a task, according to an exemplary embodiment.

The health care device 100 may evaluate the task, and change the task according to the evaluation. FIG. 8 is a flowchart illustrating a method of operating the health care device 100 that evaluates a task, according to an exemplary embodiment.

The controller 160 may calculate a correlation between the task and the health status by using the achievement rate (operation S810). In some exemplary embodiments, the controller 160 may calculate the correlation only when the achievement rate is equal to or above a predetermined value. The predetermined value may be a value at which the task is expected to affect the health status. For example, when the user has exercised once a week even though exercising twice a week may reduce weight, the controller 160 may not calculate a correlation between the task and the health status.

When the achievement rate is greater than the predetermined value, the health care device 100 may obtain health status information. The health status information is related to the task. For example, when the task is reducing body fat, the health care device 100 may detect bio-impedance, obtain a body fat value from the bio-impedance, and thereby obtain the health status information.

Furthermore, the controller 160 may compare previous health status information and currently obtained health status information and thereby calculate a correlation that indicates a degree of an effect of the task on a change in the health status. The correlation may be digitized. For example, when the correlation is a positive value, the achievement rate has a positive effect on the health status, and when the correlation is a negative value, the achievement rate has a negative effect on the health status. Also, when an absolute value of the correlation is large, the achievement rate has a large effect on the health status. For example, when a correlation between jogging and blood pressure is +5 and a correlation between jogging and body fat is +10, jogging has a greater effect on the body fat than blood pressure. Also, when a correlation between jogging in the morning and blood pressure is −5 and a correlation between jogging at night and blood pressure is +5, jogging in the morning has a negative effect on the blood pressure whereas jogging at night has a positive effect on the blood pressure.

When the correlation is equal to or greater than a reference value (operation S820—Yes), the controller 160 may continue monitoring whether the user achieves a task or not (operation S830). The reference value may be a predetermined value at which the task affects the health status. For example, supposing that the reference value is 7, when a correlation is +8, the controller 160 may determine that the task has a positive effect on the health status, but when the correlation is +5, the controller 160 may determine that the task has a positive effect on the health status but the effect is not enough to change the health status. Also, when the correlation is −5, the controller 160 may determine that the task has a negative effect on the health status.

However, when the correlation is below the reference value (operation S820—No), the controller 160 may finish task monitoring (operation S840). An effect of the task on the health status may vary according to individuals. For example, even though a task such as jogging is effective in reducing weight according to statistics, jogging may not be effective in reducing the weight of a certain user. Therefore, when the correlation is below the reference value, the controller 160 may provide a notification indicating that a task being executed does not affect the health status and finish task monitoring. Also, when the user maintains the health status within a normal range by achieving the task, the correlation between the achievement rate and the health status may be below the reference value. In this case, the task does not affect the health status. Therefore, the controller 160 may finish task monitoring. In addition, the controller 160 may provide another task that may improve current health status. Since the method of providing the task has been described above with reference to FIG. 4, redundant descriptions thereof are not provided below.

Even when the correlation between the achievement rate and the health status is equal to or greater than the reference value, the controller 160 may finish task monitoring when another type of health status is negatively affected. Also, in this case, another task may be provided. For example, a task such as "outdoor jogging" may have a positive effect on reducing weight but have a negative effect on health status such as a hydration level due to lack of hydration. In this case, the controller 160 may provide a notification indicating that the hydration level has been decreased due to outdoor jogging, and change the task to indoor jogging from outdoor jogging and/or provide an additional task of drinking water. As another example, when a start time of a task such as jogging is set as dawn and a user to achieve the task has high blood pressure, the controller 160 may recommend to change to a different time.

As described above, the health care device may be formed as a plurality of devices. For example, the health care device may be provided as a slave device that detects the biosignal information and provides a notification for achieving a task, and a master device that obtains the health status information from the biosignal information and provides a task, and monitors whether the task is achieved. The slave device and the master device may be wired or connected wirelessly. For example, the slave device and the master device may communicate within short distances via Bluetooth or Wi-Fi, or via mobile communication networks.

The slave device may be a device that may be worn by the user (wearable device). For example, the slave device may be a wristband type device that may be attached to and detached from a wrist of the user. The master device may be a mobile phone, a smart phone, a desktop computer, a laptop computer, a tablet personal computer (PC), a PC, an e-book terminal, a digital broadcast terminal, a Personal Digital Assistant (PDA), a television (TV), a smart TV, an Internet Protocol TV (IPTV), a Digital TV (DTV), or a server for managing health, but is not limited thereto.

Figure 9:
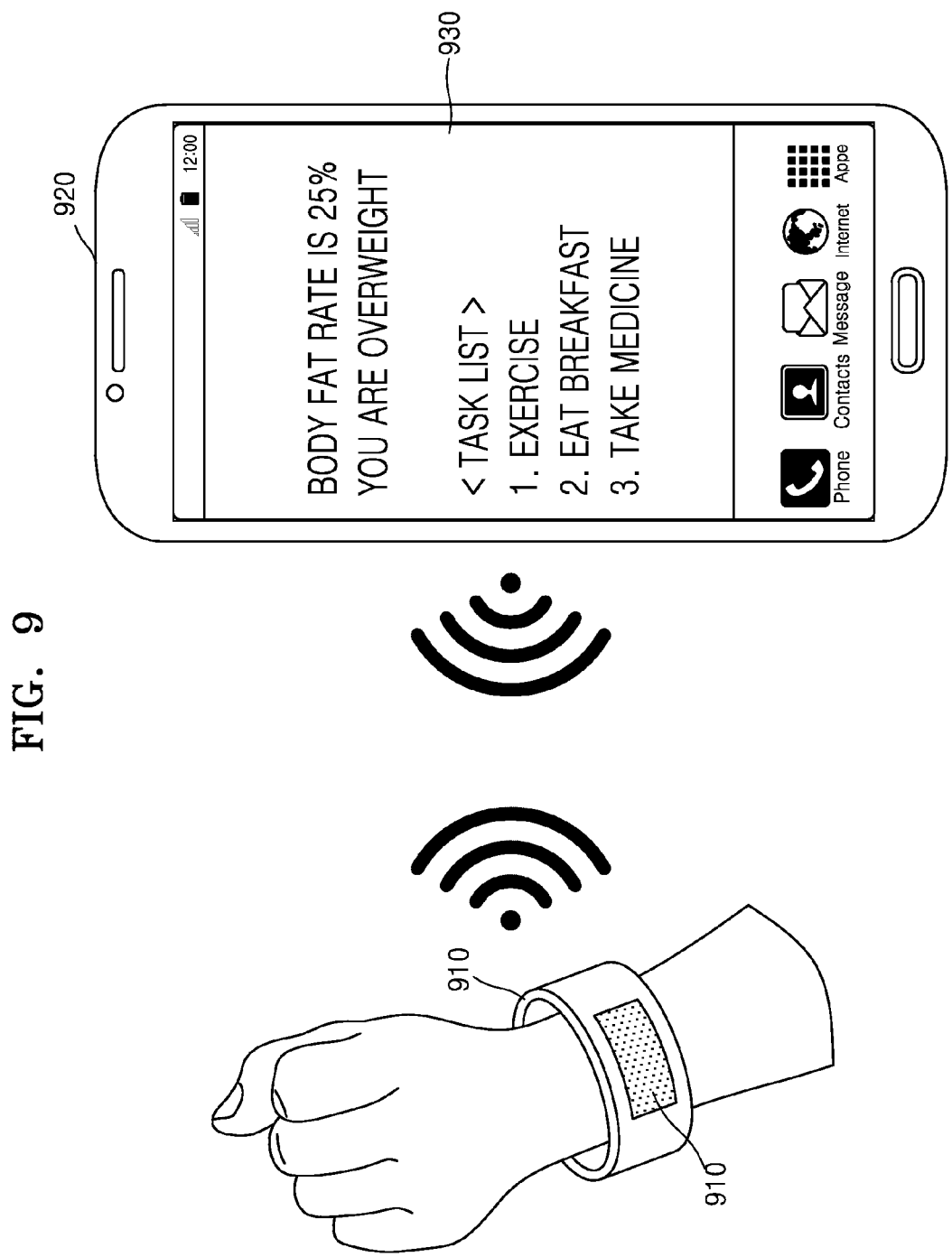
FIG. 9 is a diagram illustrating an example of a slave and a master, according to an exemplary embodiment.
Figure 10:
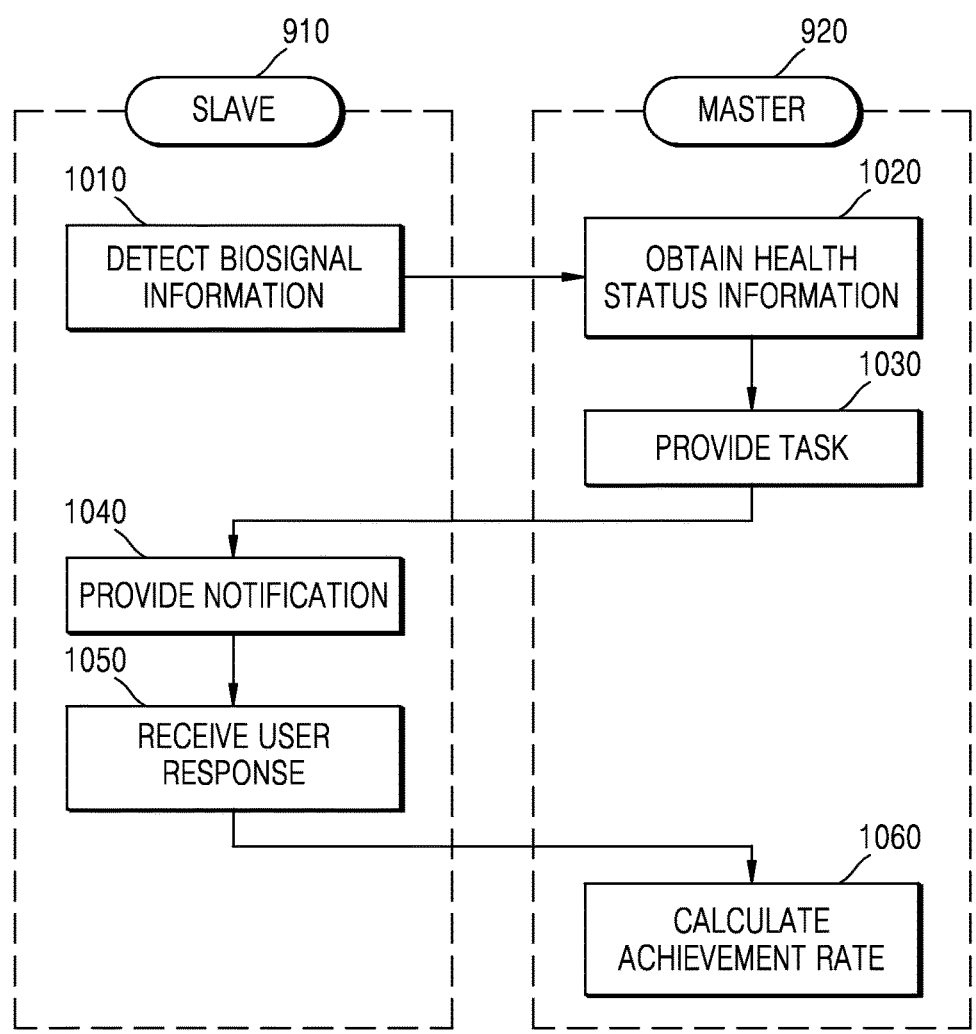
FIG. 10 is a diagram illustrating a method of providing a task by using a slave and a master, according to an exemplary embodiment.

FIG. 9 is a diagram illustrating an example of the slave device 910 and the master device 920, according to an exemplary embodiment. FIG. 10 is a diagram illustrating a method of providing a task by using the slave device 910 and the master device 920, according to an exemplary embodiment.

Referring to FIG. 9, when the slave device 910 is capable of wireless communication such as Bluetooth, Wi-Fi, Near Field Communication (NFC), etc., the slave device 910 may wirelessly communicate with the master device 920. A sensor 911 that detects biosignal information may be disposed in the slave device 910, and a display unit (e.g., display) may be disposed in the master device 920.

Referring to FIG. 10, the sensor 911 in the slave device 910 may detect biosignal information through the skin of the user (operation S1010).

The slave device 910 may transmit the detected biosignal information to the master device 920, and the master device 920 may obtain health status information by using the biosignal information (operation S1020).

Then, the master device 920 may provide a task for improving a health status (operation S1030). As shown in FIG. 9, by using the biosignal information detected by the slave device 910, the master device 920 may provide a task 930 for improving the health status. The user may set details of the task 930 via the master device 920.

Whether the task is achieved may be monitored by an interaction between the master device 920 and the slave device 910. For example, the slave device 910 may provide a notification for achieving the task (operation S1040), and receive a user response regarding the task 930 from the user (operation S1050). Also, the user response may be transmitted to the master device 920.

The master device 920 may calculate an achievement rate by using the user response (operation S1060). In addition, the master device 920 may calculate a correlation between the task and the health status or provide a task that is appropriate for each individual. As described above, when the health care device 100 is formed or provided as the slave device 910 and the master device 920, a task may be appropriately provided for a health status regardless of a limitation due to, for example, a screen size or processing capability of the slave device 910. Also, since the master device 920 performs signal processing that uses a large amount of data, a size and signal process capacity of the slave device 910 may be reduced.

Figure 11:
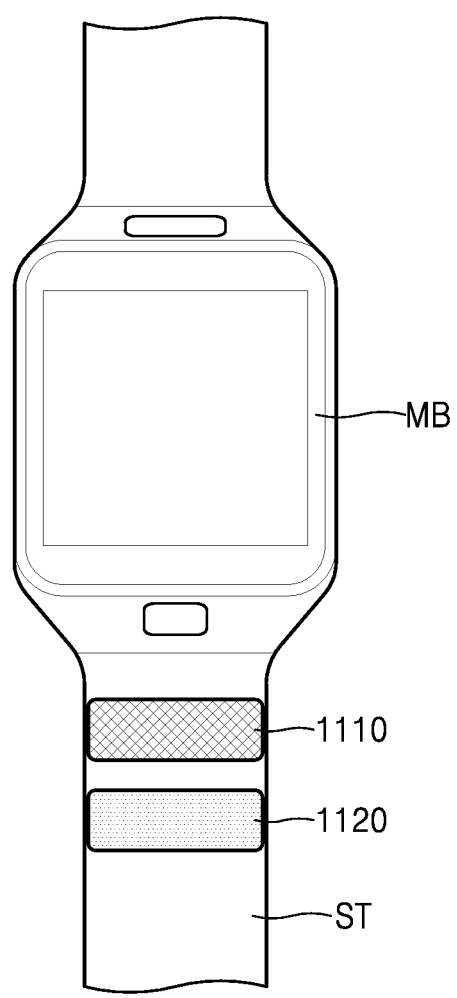
FIG. 11 is a diagram of a wristband type device capable of monitoring whether a task is finished, according to an exemplary embodiment.

FIG. 11 is a diagram of a wristband type device capable of monitoring whether a task is finished, according to an exemplary embodiment. As shown in FIG. 11, the wristband type device may include a main body MB and a strap ST. The strap ST is connected to both sides of the main body MB such that the wristband type device may be worn on a wrist of the user. The wristband type device may include a plurality of modules that may monitor whether a task is achieved or finished. For example, the strap ST may include a first module 1110 that provides a task start notification and a second module 1120 that receives from the user a user response regarding whether a task is achieved. As described above, since the first and second modules 1110 and 1120 are disposed at the strap ST, the main body MB does not have to be activated to monitor whether or not the user has achieved or finished the task. Therefore, the wristband type device may consume less power.

Also, the first and second modules 1110 and 1120 may be formed as a single module. Therefore, since providing of a notification and reception of a user response may be performed in a single module, the wristband type device may be more intuitive for the user. At least one of colors and shapes of modules, colors of emitted light in modules, and light emission frequencies in modules may be provided differently according to types of tasks so that the tasks may be easily distinguished.

Also, a module may be assigned for each task, provide an alarm to the user to start a task, and receive a user response regarding whether the task is achieved from the user. For example, when an exercise habit and an eating habit are included in tasks to be achieved, a module for adjusting the exercise habit and a module for adjusting the eating habit may be provided separately.

Also, the first module 1110 and the second module 1120 may be constituted as an accessory separate from the wristband type device, and may be attached on and detached from the strap ST. At least one of the first module 1110 and the second module 1120 may include a communicator and transmit and receive information to and from the wristband type device 1100.

While not restricted thereto, an exemplary embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an exemplary embodiment may be written as a computer program transmitted over a computer-readable transmission medium, such as a carrier wave, and received and implemented in general-use or special-purpose digital computers that execute the programs. Moreover, it is understood that in exemplary embodiments, one or more units or components of the above-described devices can include circuitry, a processor, a microprocessor, etc., and may execute a computer program stored in a computer-readable medium.

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. A method of operating a health care device, the method comprising:
   detecting, by a sensor of the health care device, biosignal information of a user through skin of the user;
   obtaining, by the health care device, health status information of the user based on the detected biosignal information;
   obtaining, by the health care device, in response to the health status information being within a reference range, a task of the user to cause the health status information to be outside of the reference range;
   providing, by the health care device, the task; and
   monitoring, by the health care device, whether the user achieves the provided task,
   wherein the monitoring comprises:
      receiving, from the user via an input to a user interface of the health care device, a user response regarding the provided task,
      calculating, by the health care device, an achievement rate of the provided task based on the received user response, and
      calculating, by the health care device, a correlation value that indicates a degree of an effect of the task on a change in the health status by comparing previous health status information and current health status information only when the achievement rate is equal to or above a predetermined value.

2. The method of claim 1, wherein the reference range includes an abnormal range corresponding to abnormal health status information.

3. The method of claim 1, wherein the providing the task comprises:
   displaying, by the health care device, one or more details of the provided task; and
   modifying at least one of the displayed one or more details according to an input of the user to the user interface of the health care device.

4. The method of claim 3, wherein the modifying comprises, in response to a modification according to the input of the user being outside a predetermined modifiable range, providing a notification indicating that the modification is outside the predetermined modifiable range.

5. The method of claim 3, wherein the modifying comprises, in response to a modification according to the input of the user being outside a predetermined modifiable range, determining a value of the one or more details to be a boundary value of the predetermined modifiable range.

6. The method of claim 3, wherein the one or more details comprise at least one of a type, a cycle, an execution amount, a start time, and an execution duration of the provided task.

7. The method of claim 1, wherein the monitoring further comprises providing an execution start notification regarding the provided task.

8. The method of claim 1, further comprising, in response to the calculated correlation value being below a reference value, stopping the monitoring of whether the user achieves the provided task.

9. The method of claim 1, wherein the biosignal information is detected in a non-invasive manner.

10. The method of claim 1, wherein:
    the biosignal information comprises at least one of blood glucose, cholesterol, bio-impedance, electrocardiogram (ECG), ballistocardiogram (BCG), photoplethysmograph (PPG), and electromyogram (EMG) of the user; and
    the health status information comprises at least one of, body fat, skeletal muscles, visceral fat, basal metabolic rate (BMR), a hydration level, triglyceride (TG), low density lipoprotein (LDL), high density lipoprotein (HDL), a ratio between LDL and HDL, a stress index, maximum blood pressure, minimum blood pressure, a fasting blood sugar level, a blood glucose increase rate, a total amount of cholesterol, and a blood glucose health index of the user.

11. The method of claim 1, wherein the provided task comprises at least one of an exercise habit, an eating habit, a sleeping habit, a medicine intake habit, and a fluid intake habit.

12. A health care device comprising:
    a sensor configured to contact skin of a user and to detect biosignal information of the user through the skin;
    at least one processor configured to obtain health status information of the user based on the detected biosignal information, and to obtain, in response to the health status information being with a reference range, a task of the user to cause the health status information to be outside of the reference range; and
    an output unit configured to output the task,
    wherein the at least one processor is configured to receive, via an input to a user interface of the health care device, a user response regarding the output task, calculate an achievement rate of the provided task based on the received user response, and calculate a correlation value that indicates a degree of an effect of the task on a change in the health status by comparing previous health status information and current health status information only when the achievement rate is equal to or above a predetermined value.

13. The health care device of claim 12, wherein the at least one processor is configured to output, via the output unit, one or more details of the output task, and to modify at least one detail selected from among the output one or more details according to an input of the user to the user interface of the health care device.

14. The health care device of claim 13, wherein in response to the task negatively affecting another type of health status other than the health status, the at least one processor is configured to provide a notification indicating that the other type of health status has been negatively affected.

15. The health care device of claim 12, wherein the health care device is a wristband type device that is attachable to and detachable from a wrist of the user.

16. The health care device of claim 12, further comprising at least one of a first module configured to provide an execution start notification regarding the output task and a second module configured to receive a user response regarding the output task.

* * * * *